United States Patent
Coppi et al.

(10) Patent No.: US 6,603,006 B2
(45) Date of Patent: Aug. 5, 2003

(54) INTERMEDIATE FOR THE SYNTHESIS OF AMLODIPINE, A PROCESS FOR THE PREPARATION THEREOF AND CORRESPONDING USE

(75) Inventors: Laura Coppi, Barcelona (ES); Yolanda Gasanz Guillén, Barcelona (ES); Julio Campón Pardo, Barcelona (ES)

(73) Assignee: Esteve Química, S.A., Barcelona (ES)

( * ) Notice: Subject to any disclaimer, the term of this patent is extended or adjusted under 35 U.S.C. 154(b) by 0 days.

(21) Appl. No.: 10/041,475

(22) Filed: Jan. 10, 2002

(65) Prior Publication Data

US 2002/0068831 A1 Jun. 6, 2002

Related U.S. Application Data

(62) Division of application No. 09/422,934, filed on Oct. 22, 1999, now abandoned.

(30) Foreign Application Priority Data

Oct. 26, 1998 (ES) .................................. 9802240

(51) Int. Cl.[7] ..................... C07D 213/12; C07D 401/12
(52) U.S. Cl. ................................ 546/250; 546/277.7
(58) Field of Search ............................. 546/250, 277.7

(56) References Cited

U.S. PATENT DOCUMENTS 5,362,729 A * 11/1994 Cozzi et al. ............. 514/235.5

FOREIGN PATENT DOCUMENTS

| EP | 60674 A | 9/1982 |
| EP | 89167 A | 9/1983 |
| EP | 116769 A | 8/1984 |
| WO | WO 88/01266 A | 2/1988 |

OTHER PUBLICATIONS

Cran and Hammond, "Organic Chemistry", McGraw Hill Book Co., NY (1964) 2nd ed, pp 565–67.*
George R. Newkome, et al, "Nicotinic Acid Crown Ethers: Synthesis, Complexation and Reduction," *Tetrahedron*, vol. 39, No. 12, 1983, pp. 2001–2008.
John E. Arrowsmith, et al, "Long–Acting Dihydropyridine Calcium Antagonists. 1. 2–Alkoxymethyl Derivative Incorporating Basic Substituents," *J. Med. Chem.*, 29, 1986, pp. 1692–1702.
A. P. Beresford, et al, "Biotransformation of Amlodipine," *Arzneim–Forsch./Drug Res.* 39 (1), Nr. 2, 1989, pp. 201–209.
D. Alker, et al, "Long–Acting Dihydropyridine Calcium Antagonists. 9. Structure Activity Relationships Around Amlodipine," *Eur. J. Med. Chem.*, 26, 1991, pp. 907–913.

Mohammad R. Marzabadi, et al, "A Double Protection Strategy for the Synthesis of 3,5–Disubstituted Dihydropyridines," *Tetrahedron Letters*, 39, 1998, pp. 5293–5296.

* cited by examiner

Primary Examiner—Patricia L. Morris
(74) Attorney, Agent, or Firm—Sughrue Mion, PLLC

(57) ABSTRACT

An intermediate for the synthesis of amlodipine, a process for the preparation thereof and the corresponding use are disclosed. The intermediate is ethyl 3-amino-4-(2-(phthalimido)ethoxy)crotonate and is of formula III:

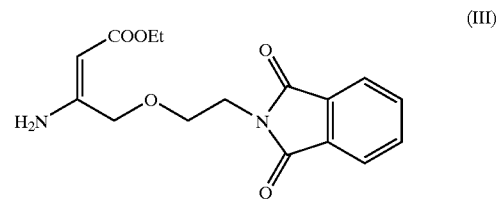

The process for the preparation thereof comprises reacting the acetoacetate of formula:

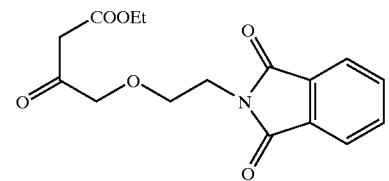

with ammonium acetate; and the use thereof is for the preparation of the compound of formula:

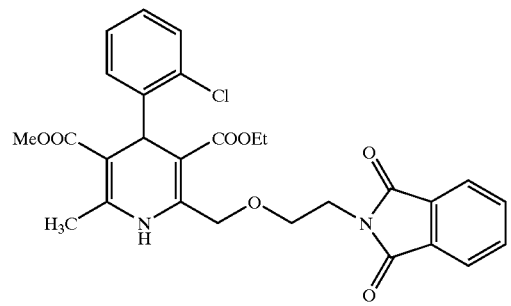

the process being conducted by reacting ethyl 3-amino-4-[2-(phthalimido)ethoxy]crotonate with a benzylidene derivative.

1 Claim, No Drawings

INTERMEDIATE FOR THE SYNTHESIS OF AMLODIPINE, A PROCESS FOR THE PREPARATION THEREOF AND CORRESPONDING USE

This is a divisional of application Ser. No. 09/422,934, filed Oct. 22, 1999, now abandoned, the disclosure of which is incorporated herein by reference.

DESCRIPTION

1. Field of the Invention

The present invention relates to an intermediate for the synthesis of amlodipine, to a process for the preparation thereof and to a use of the intermediate.

The invention belongs to the field of heterocyclic chemistry and, as indicated, it relates to a chemical intermediate, ethyl 3-amino-4-(2-(phthalimido)ethoxy)crotonate, to the process for the preparation thereof, and to the use thereof for the synthesis of 2-((2-aminoethoxy)methyl)-4-(2-chlorophenyl)-3-ethoxycarbonyl-5-methoxycarbonyl-6-methyl-1,4-dihydropyridine, generically known as amlodipine, a product having a therapeutical activity used as an antiischaemic and antihypertensive agent.

2. Prior Art

Patent EP 0 089 167 discloses the use of 1,4-dihydropyridines of formula I, as immediate precursors of amlodipine of formula II:

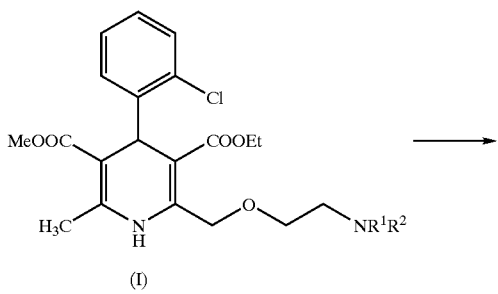

$NR^1R^2$=protected amine group

Patent EP 0 060 674 discloses two processes for the preparation of 1,4-dihydropyridines containing in the 2 position a substituent having an amino group and having antiischaemic and antihypertensive utility. In both cases, the yields indicated are very low (~15%) and the products have to be purified by chromatography, making the industrial application thereof difficult.

Patent EP 0 089 167 discloses the preparation of various 1,4-dihydropyridines of formula I, precursors of amlodipine, following the same processes as indicated in patent EP 0 060 674:

(a) where the aminoprotector groups are benzyl, azido or phthalimido, by reacting 2-chlorobenzaldehyde (IV) with ethyl acetoacetate (V) and methyl 3-aminocrotonate (VI)

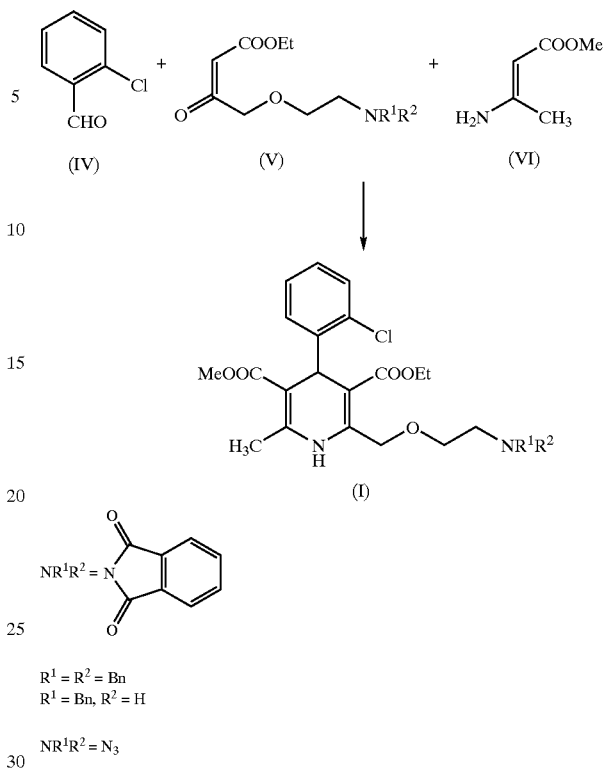

$R^1 = R^2 = Bn$
$R^1 = Bn, R^2 = H$ $NR^1R^2 = N_3$ (b) Alternatively, where the aminoprotector groups are benzyl and azido, by reacting the benzylidene derivative (VII) with the aminocrotonate (VIII), this latter being prepared "in situ" from the corresponding ethyl acetoacetate (V) and ammonium acetate.

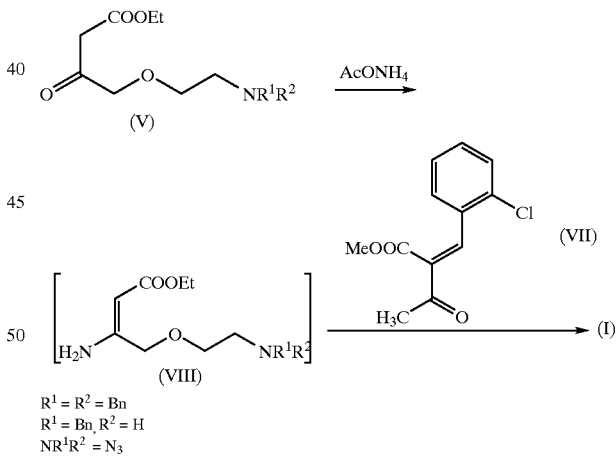

$R^1 = R^2 = Bn$
$R^1 = Bn, R^2 = H$
$NR^1R^2 = N_3$

In both processes the yields obtained are very low (30% and 11% respectively where the protector group is azido, $NR^1R^2=N_3$). On the other hand, the intermediate aminocrotonates (VIII) are not isolated or characterized, since they are prepared "in situ" from the corresponding ethyl acetoacetate (V) prior to the reaction with the benzylidene derivative (VII). No description has been found in the literature for the isolation or characterisation of these aminocrotonates (VIII). The present inventors have unsuccessfully tried to isolate the formula VIII compound disclosed in patent EP 0 089 167, where $R^1=R^2=Bn$. This patent discloses these compounds as prepared "in situ" (page 8), without any experimental check of their characteristics or chemical structure.

Since the acetoacetates (V) and the benzylidene derivative (VII) are oils, it was fundamental to have a solid intermediate allowing formula (I) compounds to be prepared with a high yield and purity.

DETAILED DESCRIPTION OF THE INVENTION

The present invention relates to a new compound, ethyl 3-amino-4-(2-(phthalimido)ethoxy)crotonate, of formula III:

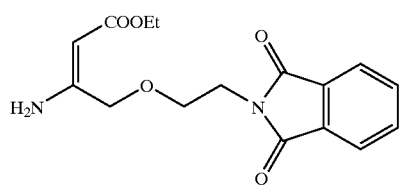

(III)

It has been possible to isolate the new compound of formula III in solid state, thereby allowing for the purification, identification and characterisation thereof. This compound has turned out to be very useful as an intermediate for the synthesis of 4-(2-chlorophenyl)-3-ethoxycarbonyl-5-methoxycarbonyl-6-methyl-2-(2-phthalimidoethoxy)methyl-1,4-dihydropyridine (of formula I, where $NR^1R^2$=phthalimido), the immediate precursor of amlodipine.

The process of preparation of III consists of reacting ethyl 4-[2-(phthalimido)ethoxy]acetoacetate (V, $NR^1R^2$=phthalimido) with ammonium acetate in a reaction medium, which is preferably an organic solvent (ethanol, isopropanol, toluene, xylene, etc.) the desired product being obtained in solid state with a good yield and a high degree of purity. The reaction is conducted at a temperature ranging from 10° C. to the reflux temperature, preferably from 50 to 70° C., and with a Dean-Stark device allowing the water formed in the reaction to be removed. At the end of the reaction, the product was crystallised in an alcohol, being isolated in solid form, the impurities remaining dissolved in the mother liquors.

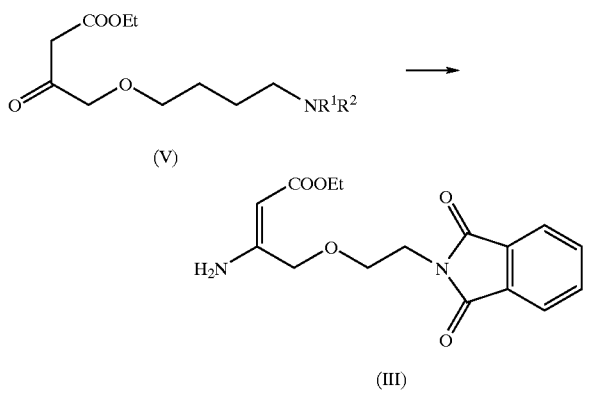

-continued

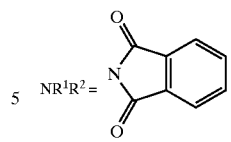

$NR^1R^2$ =

One use of interest of the solid ethyl 3-amino-4-(2-(phthalimido)ethoxy)crotonate (of formula III) is achieved by reacting it with methyl 2-(2-chloro-benzylidene)acetoacetate (of formula VII) in a organic solvent (methanol, ethanol, isopropanol, toluene, xylene), preferably ethanol, at a temperature ranging from 10° C. and the reflux temperature, preferably from 60 to 80° C. The reaction was held for 12 to 24 hours, after which, it was cooled, whereby the 4-(3-chlorophenyl)-3-ethoxycarbonyl-5-methoxycarbonyl-6-methyl-2-(2-phthalimidoethoxy)methyl-1,4-dihydropyridine (I; $NR^1R^2$=phthalimido) crystallised, and was isolated with a high degree of purity and yield, superior to those described in the literature.

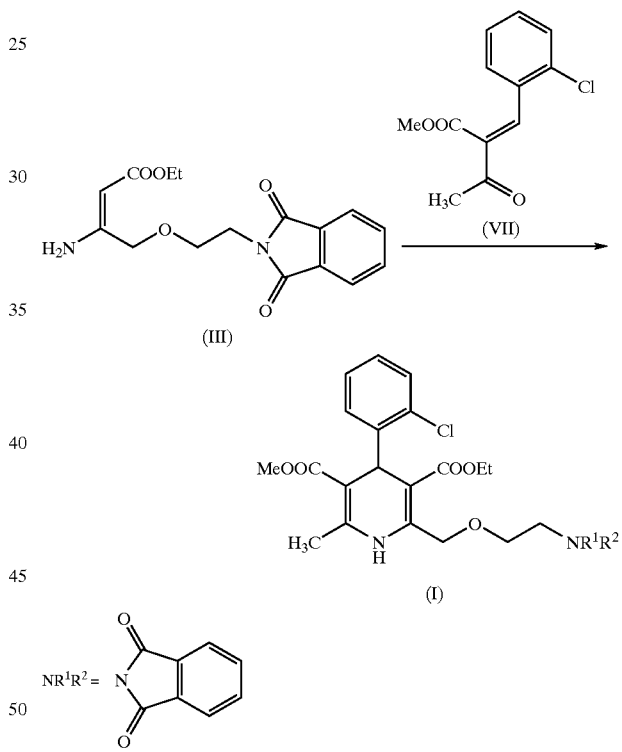

Certain examples illustrating the invention are described hereinafter.

EXAMPLE 1

Ethyl 3-amino-4-(2-(phthalimido)ethoxy)crotonate (III)

32 g (100 mmoles) of ethyl 4-[2-(phthalimido)ethoxy]acetoacetate in 200 ml of toluene were reacted with 8.1 g (105 mmoles) of ammonium acetate at 65° C. for 4 hours, the water formed in the reaction being removed with a Dean-Stark apparatus. The toluene was evaporated to dryness and the distillation residue was crystallised from isopropanol to give 24.5 g (yield 77%) of a beige coloured solid, corresponding to ethyl 3-amino-4-(2-(phthalimido)ethoxy)crotonate.

m.p.:90–92° C. IR(KBr): 3460, 3343, 1769, 1702, 1674, 1618, 1571, 1430, 1398, 1364, 1354, 1158, 1125, 1031, 721 cm$^{-1}$ $^{1}$H NMR (300 MHz, DMSO) δ7.8 (m, 4H, ar), 7.5 (s, 1H, NH$_2$), 6.7 (s, 1H, NH$_2$), 4.4 (s, 1H, —CH═), 3.9 (m, 4H, —COCH$_2$—, ═C—CH$_2$O—), 3.8 (t, 2H, —OCH$_2$—), 3.6 (t, 2H, —CH$_2$N), 1.1 (t,3H, CH$_3$)

EXAMPLE 2

4-(2-chlorophenyl)-3-ethoxycarbonyl-5-methoxycarbonyl-6-methyl-2-(2-phthalimidoethoxy)methyl-1,4-dihydropyridine 24.0 g (75.4 mmoles) of ethyl 3-amino-4-(2-(phthalimido)ethoxy)crotonate and 18.9 g (79.2 mmoles) of methyl 2-(2-chlorobenzylidene)acetoacetate in 64 ml of ethanol were heated under reflux for 20 hours. The reaction mixture was diluted with 56 ml of ethanol and was cooled to crystallise the product. 14.2 g (yield 70%) of 4-(2-chlorophenyl)-3-ethoxycarbonyl-5-methoxycarbonyl-6-methyl-2-(2-phthalimidoethoxy)methyl-1,4-dihydropyridine were obtained.

m.p.: 150–151° C.

IR (KBr): 3370, 1712, 1489, 1422, 1392, 1287, 1201, 1122, 1102, 1024 cm$^{-1}$.

What is claimed is:
1. A process for preparation for formula:

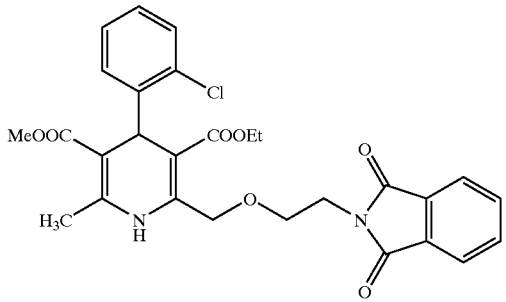

comprising dissolving solid ethyl 3-amino-4-(2-(phthalimido)ethoxy)crotonate of formula III:

(III)
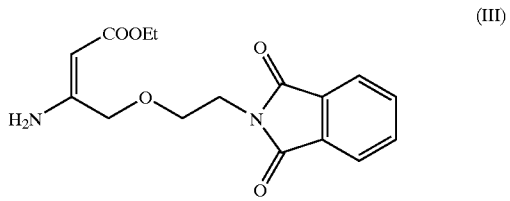

in an organic solvent, and reacting ethyl 3-amino-4-(2-(phthalimido)ethoxy)crotonate of formula III with a benzylidene derivative of formula VII:

(VII)
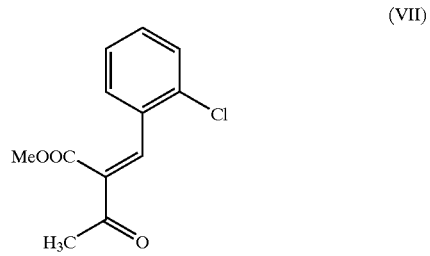

* * * * *